US009120660B2

(12) United States Patent
Sangi et al.

(10) Patent No.: US 9,120,660 B2
(45) Date of Patent: *Sep. 1, 2015

(54) METHOD AND APPARATUS FOR THE CLEANING OF CONTAINERS SUCH AS PLASTIC BOTTLES IN A BOTTLE FILLING PLANT OR CONTAINERS IN A CONTAINER FILLING PLANT

(75) Inventors: Daryoush Sangi, Hamburg (DE); Thomas Herold, Ahrensburg (DE)

(73) Assignee: KHS GmbH, Dortmund (DE)

( * ) Notice: Subject to any disclaimer, the term of this patent is extended or adjusted under 35 U.S.C. 154(b) by 857 days.

This patent is subject to a terminal disclaimer.

(21) Appl. No.: 12/605,550

(22) Filed: Oct. 26, 2009

(65) Prior Publication Data

US 2010/0276028 A1 Nov. 4, 2010

Related U.S. Application Data

(63) Continuation-in-part of application No. PCT/EP2008/003247, filed on Apr. 23, 2008, and a continuation-in-part of application No. PCT/EP2008/002858, filed on Apr. 11, 2008.

(30) Foreign Application Priority Data

Apr. 27, 2007 (DE) .......................... 10 2007 020 457
Apr. 27, 2007 (DE) .......................... 10 2007 020 458

(51) Int. Cl.
*B65B 55/10* (2006.01)
*A61L 2/20* (2006.01)
(Continued)

(52) U.S. Cl.
CPC ................. *B67C 7/0073* (2013.01); *A61L 2/18* (2013.01); *A61L 2/208* (2013.01); *B08B 9/26* (2013.01); *B65B 55/10* (2013.01)

(58) Field of Classification Search
CPC ................................. B65B 55/10; A61L 2/208
USPC ........ 423/272, 273; 422/28, 29, 30, 292, 302, 422/105, 108, 110; 53/253, 331.5, 317, 53/319, 426
See application file for complete search history.

(56) References Cited

U.S. PATENT DOCUMENTS 2,123,145 A * 7/1938 Peiler .............................. 65/262
2,974,446 A * 3/1961 Poting ............................. 65/227
(Continued)

FOREIGN PATENT DOCUMENTS

DE   198 46 322 A1   4/2000
DE   199 49 692       4/2001
(Continued)

OTHER PUBLICATIONS

Russian Office Action 2009143814/15(062359).
(Continued)

*Primary Examiner* — Stephen F Gerrity
*Assistant Examiner* — Joy N Sanders
(74) *Attorney, Agent, or Firm* — Nils H. Ljungman & Associates

(57) ABSTRACT

Method and apparatus for sterilizing containers with a sterilization medium. The method involves first introducing a sterilization medium into a container, and then introducing a heated gaseous and/or vaporous activation medium into the container. The activation medium is used to heat and activate the sterilization medium to destroy microorganisms. The temperature of the heated gaseous and/or vaporous activation medium is controlled based on the detected temperature of the container or the wall of the container.

18 Claims, 6 Drawing Sheets

(51) Int. Cl.
  *B67C 7/00*   (2006.01)
  *A61L 2/18*   (2006.01)
  *B08B 9/26*   (2006.01)

(56) References Cited

U.S. PATENT DOCUMENTS

| | | | |
|---|---|---|---|
| 4,354,095 A * | 10/1982 | de Vries | 219/388 |
| 5,398,734 A | 3/1995 | Hartel | |
| 6,702,985 B1 | 3/2004 | Taggart et al. | |
| 2002/0029543 A1* | 3/2002 | Taggart | 53/426 |
| 2002/0168289 A1 | 11/2002 | McVey | |
| 2004/0191112 A1 | 9/2004 | Hill et al. | |
| 2006/0005896 A1 | 1/2006 | Till | |
| 2006/0032189 A1 | 2/2006 | Giacobbe | |

FOREIGN PATENT DOCUMENTS

| | | |
|---|---|---|
| DE | 199 49 692 A1 | 4/2001 |
| DE | 10 2004 030 956 | 1/2006 |
| DE | 10 2004 030 956 A1 | 1/2006 |
| DE | 10 2004 030957 A1 | 1/2006 |
| DE | 10 2005 018 382 A1 | 10/2006 |
| EP | 0 590 505 | 4/1994 |
| EP | 0 590 505 A1 | 4/1994 |
| JP | 2003512260 | 4/2003 |
| JP | 2006-509690 | 3/2006 |
| JP | 2006509690 | 3/2006 |
| WO | WO 2006/053745 A1 | 5/2006 |
| WO | WO 2007/134803 | 11/2007 |

OTHER PUBLICATIONS

International Search Report PCT/EP2008/0031247 and English translation thereof.
German Search Report 10 2007 020 457.6.

* cited by examiner

METHOD AND APPARATUS FOR THE CLEANING OF CONTAINERS SUCH AS PLASTIC BOTTLES IN A BOTTLE FILLING PLANT OR CONTAINERS IN A CONTAINER FILLING PLANT

CONTINUING APPLICATION DATA

This application is a Continuation-In-Part application of International Patent Application No. PCT/EP2008/003247, filed on Apr. 23, 2008, which claims priority from Federal Republic of Germany Patent Application No. 10 2007 020 457.6, filed on Apr. 27, 2007. International Patent Application No. PCT/EP2008/003247 was pending as of the filing date of this application. The United States was an elected state in International Patent Application No. PCT/EP2008/003247.

This application is also a Continuation-In-Part application of International Patent Application No. PCT/EP2008/002858, filed on Apr. 11, 2008, which claims priority from Federal Republic of Germany Patent Application No. 10 2007 020 458.4, filed on Apr. 27, 2007. International Patent Application No. PCT/EP2008/002858 was pending as of the filing date of this application. The United States was an elected state in International Patent Application No. PCT/EP2008/002858.

BACKGROUND

1. Technical Field

The present application pertains to a method and apparatus for the cleaning of containers such as plastic bottles in a bottle filling plant or containers in a container filling plant.

2. Background Information

Background information is for informational purposes only and does not necessarily admit that subsequently mentioned information and publications are prior art.

A beverage bottling plant for filling bottles with a liquid beverage filling material can possibly comprise a beverage filling machine, which is often a rotary filling machine, with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material.

Some beverage bottling plants may possibly comprise filling arrangements that receive a liquid beverage material from a toroidal or annular vessel, in which a supply of liquid beverage material is stored under pressure by a gas. The toroidal vessel may also be connected to at least one external reservoir or supply of liquid beverage material by a conduit or supply line. In some circumstances it may even be possible that a beverage bottling plant has two external supply reservoirs, each of which may be configured to store either the same liquid beverage product or different products. These reservoirs could possibly be connected to the toroidal or annular vessel by corresponding supply lines, conduits, or other arrangements. It is also possible that the external supply reservoirs could be in the form of simple storage tanks, or in the form of liquid beverage product mixers.

A wide variety of types of filling elements are used in filling machines in beverage bottling or container filling plants for dispensing a liquid product into bottles, cans or similar containers, including but not limited to filling processes that are carried out under counterpressure for the bottling of carbonated beverages. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine.

After a filling process has been completed, the filled beverage bottles are transported or conveyed to a closing machine, which is often a rotary closing machine. A revolving or rotary machine comprises a rotor, which revolves around a central, vertical machine axis. There may further be provided a conveyer arrangement configured to transfer filled bottles from the filling machine to the closing station. A transporting or conveying arrangement can utilize transport star wheels as well as linear conveyors. A closing machine Closes bottles by applying a closure, such as a screw-top cap or a bottle cork, to a corresponding bottle mouth. Closed bottles are then usually conveyed to an information adding arrangement, wherein information, such as a product name or a manufacturer's information or logo, is applied to a bottle. A closing station and information adding arrangement may be connected by a corresponding conveyer arrangement. Bottles are then sorted and packaged for shipment out of the plant.

Many beverage bottling plants may also possibly comprise a rinsing arrangement or rinsing station to which new, non-return and/or even return bottles are fed, prior to being filled, by a conveyer arrangement, which can be a linear conveyor or a combination of a linear conveyor and a starwheel. Downstream of the rinsing arrangement or rinsing station, in the direction of travel, rinsed bottles are then transported to the beverage filling machine by a second conveyer arrangement that is formed, for example, by one or more starwheels that introduce bottles into the beverage filling machine.

It is a further possibility that a beverage bottling plant for filling bottles with a liquid beverage filling material can be controlled by a central control arrangement, which could be, for example, a computerized control system that monitors and controls the operation of the various stations and mechanisms of the beverage bottling plant.

The sterilization of packaging containers of the type used in the food and beverage industry, for example, is becoming increasingly important because a long shelf life of the contents of the container without the addition of preservatives or a subsequent treatment, e.g. by pasteurization, is becoming increasingly unattractive on account of its negative effect on the packaged product.

To prevent, restrict, and/or minimize this, for example, aseptic filling machines are used to fill bottles. For this purpose, the entire bottling plant or a portion of the bottling plant may be operated in a sterile environment. To achieve this sterile environment, the plant may be enclosed in a housing, the interior is sterilized and kept as sterile as possible, and steps are taken to essentially ensure or promote that the air and all or most other substances that are introduced into the interior are practically sterile. An essential component of this process is also that the interior of the containers to be filled are also sterilized.

Containers, for example beverage bottles, cans, medicament or medicine bottles, or medicament or medicine cans, must or should often be sterilized prior to filling so as to prevent, restrict, and/or minimize the material to be filled from spoiling or going bad. In the cooperation with the aseptic treatment installations or aseptic treatment stations and the filling installations or filling stations, filling of the containers can occur thus under clean room or clean space conditions by means of which a subsequent sterilization, e.g. by heating of the container together with the container contents, can be avoided, restricted, and/or minimized, which is desirable under certain circumstances as pertains to the quality and/or the taste of the filling material or the bottled material.

Some methods for the sterilization of bottles, cans or similar containers make use of a sterilization medium comprising hydrogen peroxide, i.e., make use of a sterilization medium (hereinafter also hydrogen peroxide sterilization medium) which comprises hydrogen peroxide in mixture with hot sterile air. In these methods, which for example are used for sterilizing of containers for beverages, but also for sterilizing containers or packages for other products, such as medicaments, when the hot hydrogen peroxide sterilization medium is brought onto the inner surface of the colder container a hydrogen peroxide condensation film is formed by condensation and this is then activated in a following activation phase by introducing a sterile hot gaseous and/or vaporous activation medium, such as by introducing hot sterile air, so that oxygen free radicals are produced by the breakdown of hydrogen peroxide and these react with the germs and impurities present to sterilize the container.

In these methods the sterile air used as activation medium may be heated to the activation temperature by conducting it through a heat exchanger heated to a temperature between one hundred thirty degrees Celsius and one hundred fifty degrees Celsius. Then, in a step following the activation phase, the containers are blown upon and cooled down with the sterile air, which is supplied to the container at a temperature distinctly below the activation temperature. For this, the sterile air is taken at a correspondingly high volume flow through the heat exchanger, preventing it from becoming heated to the activation temperature.

Furthermore, some methods and devices treat bottles or such containers with a hot treatment medium, which is introduced into the containers. Thanks to temperature sensors, the temperature of the containers is detected before and after the heat treatment, or the temperature of the treatment medium flowing back out, and the temperature of the hot treatment medium and/or the intensity of the treatment is controlled as a function of the measured temperatures. No treatment with a treatment medium comprising hydrogen peroxide is mentioned.

OBJECT OR OBJECTS

An object of the present application is to provide a method and a device whereby, while maintaining a high rate of degermination, i.e., a high quality of sterilization, the treatment time as a whole and in at least one possible embodiment the duration of the activation phase can be reduced, and this with gentle treatment of the containers.

SUMMARY

To solve this object, a method is designed for the sterilization of bottles, cans or similar containers by introducing a hot hydrogen peroxide sterilization medium into the containers in an application phase and by activation of the hydrogen peroxide sterilization medium in an activation phase by introducing a sterile gaseous and/or vaporous hot activation medium, in one possible embodiment by introducing hot sterile air into the respective container. The activation phase has at least two activation steps and in at least in the last activation step in terms of time the temperature of the volume flow of the activation medium supplied to the respective container is regulated as a function of the container temperature or the temperature of the wall of the container. The device is configured for containers such as bottles, cups, cans and the like, to carry out the method according to the present application, with at least one activator head for introducing the hot activation medium into the containers. The device comprises at least one device for noncontact temperature measurement of surfaces of solid bodies and an interconnected computer-supported control and regulation mechanism, and this for evaluation of measured values and for regulation of the temperature and/or volume flow of the activation medium supplied to the respective container at least in a last activation step in time of an activation phase having at least two activation steps as a function of the container temperature or the temperature of the wall of the container. The present application indicates variant embodiments.

With the method and device of the present application, one achieves a substantial reduction in the duration of the method and in one possible embodiment the overall duration of the activation phase. At the same time, there is also a gentle treatment, avoiding thermal overstressing of the containers, with high quality of sterilization or high rate of destruction of germs. The method of the present application is therefore in one possible embodiment suitable for containers made of plastic, such as PET.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

Modifications of the present application are disclosed according to the present application. The present application is explained more closely hereafter in conjunction with the figures by a sample embodiment. There are shown.

DESCRIPTION OF EMBODIMENT OR EMBODIMENTS

Figure 1:
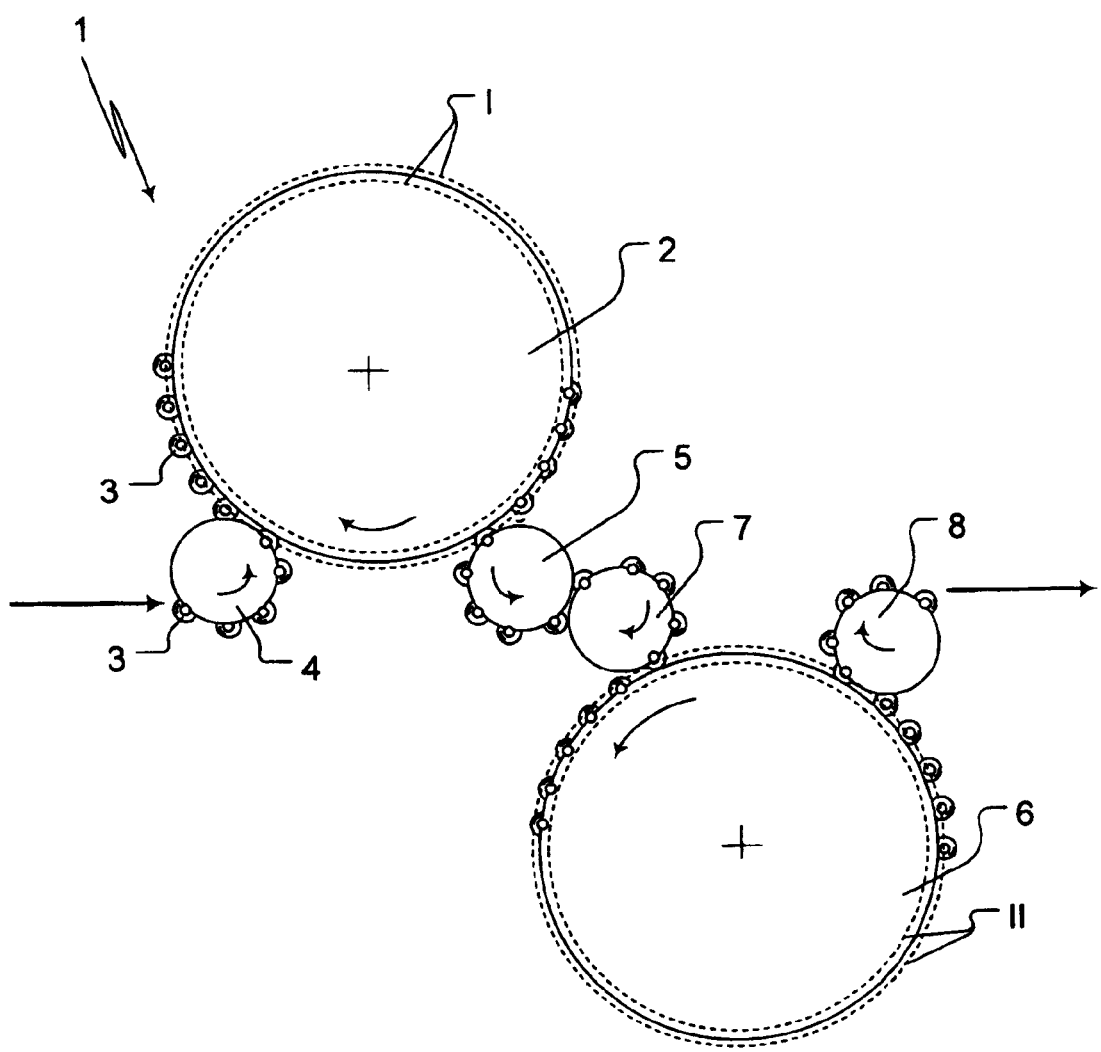
FIG. 1 in very simplified representation and in top view, a machine or device for carrying out the method of the present application.

Disclosed herein is a method for the sterilization of bottles, cans or similar containers by introducing a hot hydrogen peroxide sterilization medium into the containers in an application phase and by activation of the hydrogen peroxide sterilization medium in an activation phase by introducing a sterile gaseous and/or vaporous hot activation medium, in one possible embodiment by introducing hot sterile air into the respective container, as well as a sterilization device for containers such as bottles, cups, cans and the like, to carry out the method according to the present application, with at least one activator head for introducing the hot activation medium into the containers.

The device, designated generally as 1 in the figures, for sterilization of bottles and the method, has a rotor 2, which can be driven in rotation about a vertical machine axis, for application of the sterilization medium in the bottles 3 being treated, which are brought up via a container entry star wheel 4, and from which the treated, or wetted bottles 3 are removed by a container exit 5 and brought to the following activator. The activator is likewise a rotor 6 which can be driven in rotation about the vertical machine axis for activation of the sterilization medium by means of sterile hot air, which is conducted into the bottles 3 being treated. The bottles 3 are brought up to the rotor 6 via a container entry star wheel 7 and the treated, or sterilized bottles 3 are removed via a container exit 8 and taken to the next step, which is generally a filling machine.

Above each bottle opening there are provided application heads on the rotor 2, in familiar fashion. These rotate with the rotor 2 and are indicated as double broken lines I. Coordinated with each application head on the rotor 2 is a bottle or container carrier 14, by which the bottle 3 is held underneath the treatment head 6 during the treatment; in the sample embodiment, this is a bottle 3 as a PET bottle, suspended by a mouth flange at the bottle side.

The wetting of the surfaces of the bottles 3 is done by use of the hydrogen peroxide sterilization medium, which is heated in familiar fashion inside the respective treatment head by spraying of hydrogen peroxide, such as thirty-five percent hydrogen peroxide, into sterile air and by heating the resulting aerosol to a temperature $T_1$ of, say, one hundred forty-five degrees Celsius.

For the treatment, hot hydrogen peroxide sterilization medium is introduced into the interior of the bottle 3, and in such a way that a hydrogen peroxide condensation film is formed by condensation on the interior of the bottle 3, which is colder than the temperature $T_1$ of the hydrogen peroxide sterilization medium. This film uniformly coats at least the entire inner surface of the respective bottle 3 with a hydrogen peroxide condensation film.

Figure 2:
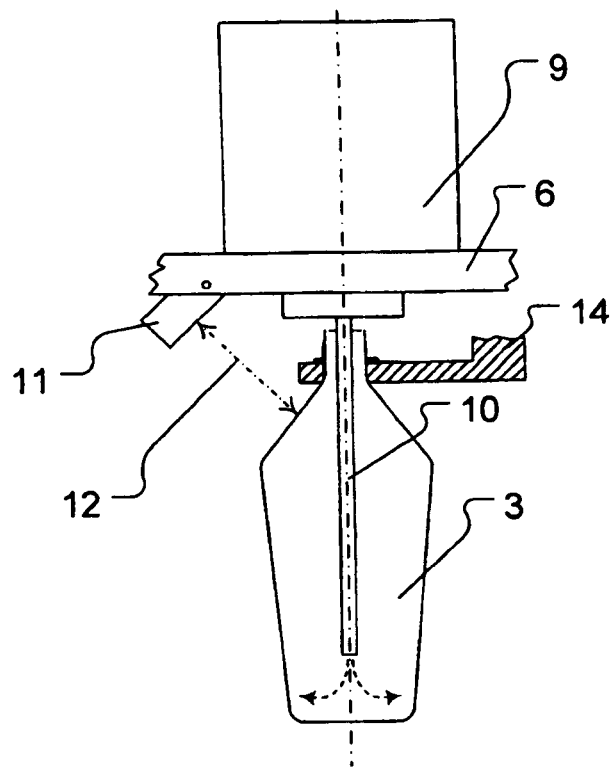
FIG. 2 in simplified representation, a treatment head of the device of FIG. 1.

After this application phase and after the bottles so wetted are taken to the rotor 6, an activation of the hydrogen peroxide condensation film occurs in another treatment phase, i.e., in an activation phase. For this, similar to the layout and arrangement on rotor 2, activator heads 9 are provided in familiar fashion above each bottle opening, which rotate with the rotor 6 and are indicated in FIG. 1 as double broken lines II. The activation is started by input of energy, namely, by bringing in a hot sterile gaseous and/or vaporous medium, such as by bringing in hot sterile air with a temperature $T_2$ into the respective bottle 3, and this by a tube 10 introduced into this bottle (FIG. 2). With this activation, a decomposition reaction of the hydrogen peroxide occurs, in the course of which oxygen free radicals are produced, which react with existing germs and/or contaminants in the bottle 3 and bring about its sterilization. The hot sterile air used in the activation phase at the same time brings about a drying of the respective bottle 3.

In the application phase, the hot hydrogen peroxide sterilization medium is brought in with a constant or substantially constant temperature $T_1$ and with a constant or substantially constant dispensing or application time, e.g., with a dispensing time of 3 seconds for bottles or containers with a volume of five hundred milliliters. The volume flow $v_1$ of the hot hydrogen peroxide sterilization medium introduced into the respective bottle 3 is likewise constant or substantially constant, for example, during the application time.

The activating of the hydrogen peroxide condensation film in the respective bottle 3 occurs during the activation phase in two process or activation steps. During a first process step, the hot sterile air used for the activation at a temperature $T_2$ is introduced into the bottle 3 with a constant or substantially constant, large volume flow $v_2$ through the tube 10 (FIG. 2). This introduction is done, for example, for a predetermined dispensing time of x seconds, or until such time as the temperature of the container wall $T_{BW}$ of the bottle 3 has reached a predetermined nominal temperature Nominal-$T_{BW}$, which is measured and monitored with a pyrometer 11 (FIG. 2). The broken-line arrow 12 indicates the measurement process. The total duration of this first process step is around eight to ten seconds.

In another, subsequent process step, the hot activation medium, in one possible embodiment being hot sterile air once again, at temperature $T_3$ and with a volume flow $v_3$ is introduced into the bottle 3 and this in the space of a dispensing time of y seconds. The temperature of the volume flow $v_3$, which is generally equal to or even lower than that of the volume flow $v_2$, is lowered as a function of the container temperature $T_{BW}$ of the bottle 3, so that during this second process step of the activation phase the container temperature $T_{BW}$ also has the nominal temperature Nominal-$T_{BW}$ or remains below a maximum permissible value. Thus, $T_3$ is less than $T_2$ and it is adjusted by a heat exchanger and/or by mixing in cold sterile air or a cold inert gas, such as $CO_2$ or $N_2$.

The nominal temperature Nominal-$T_{BW}$ in both process steps lies below a temperature that would lead to an excessive stress or deformation or a damaging of the bottles 3.

The container temperature $T_{BW}$ is also measured in the second process step in a noncontact manner, using at least one pyrometer 11, as indicated in FIG. 2. Depending on the design of the rotor 6 and its corresponding activator head, as well as the material of the container, other noncontact heat metering systems can also be used. In the variant shown in FIG. 2, the pyrometer 11 is swivel mounted so as to be optimally oriented depending on the geometry of the bottle or container.

Since the temperature of the bottle wall is monitored, one can select a steep heating gradient and temperature in the second activation phase, such as cannot be used in some instances for safety reasons (deformation of the bottle).

One advantage of at least one embodiment of a method of the present application is that the activation has a much more vigorous course and can be held at very high level, so that a substantial shortening of the length of the treatment is possible, such that, for example, a shortening to below ten seconds occurs. In one possible embodiment in the high performance range, i.e., high performance of the layout with the device 1 (number of bottles 3 processed per unit of time), in which thus far an additional, second activator was required and/or desired after the rotor 6, one can now carry out the activation phase solely at the rotor 6, or the rotor 6 can have a much smaller diameter when two activation rotors need to be provided or may be provided. This also means that a substantial increase in machine power is possible with reduced machine expense. In at least one possible embodiment, the application phase and the activation phase can be carried out on a single rotor.

Since at least one possible embodiment of a method of the present application is based on an automatic regulation of at least the volume flow $v_3$ of the activator gas being cooled by means of direct or indirect cooling in the second process step of the activation phase, time-consuming adjustments or trials to achieve an optimal or predetermined level of sterilization of bottles or similar containers do not have to be carried out by the operator of the plant. Instead, the plant can be set up and operated on the basis of manufacturer specifications, which take into account different container shapes and/or materials, and the activation phase or the process steps there may be automatically carried out and regulated by the internal control system of the plant.

In one variant of the sterilization device of the present application (not shown), rotor 6 (activator rotor) cooling sleeves are provided, which enclose the container being processed at least partially and at least part of the time during the activation. The cooling sleeve does not lie against the container surface, or if so on a portion of the surface, so that an annular gap or channels are formed between container and sleeve when operating according to design, through which a gas or a liquid can flow. In at least one possible embodiment of the present application, the sleeves are designed so that they have at least one opening, which is connected to a conduit and a gas delivery device, by which a gaseous and/or liquid medium can be conducted into the annular gap or the channels for the cooling of the wall of the container. Alternatively, cooler room or ambient air can also be brought into the annular gap or the channels through the opening and suitable conduits and vacuum pumps to cool the container wall and then be taken away. With such a cooling sleeve, a safety cooldown can be performed very quickly or the time lag of the temperature control can be shortened.

The possible parameters of one embodiment of the method of the present application for sterilization of bottles 3 with a volume of five hundred milliliters can be summarized as follows:

Application Phase

| | |
|---|---|
| Hydrogen peroxide concentration in the hydrogen peroxide sterilization medium: | 20% |
| maximum container temperature $T_{BW}$: | around 35° C.-42° C. |
| temperature $T_1$: | around 145° C. |
| pressure of hydrogen peroxide sterilization medium: | around 0.7 bar |
| volume flow $v_1$: | around 1.5 liter/bottle |
| volume flow $v_2$: | around 2.7 Nm³/h |

Activation Phase—Process Step 1

| | |
|---|---|
| maximum container temperature $T_{BW}$: | around 67° C.-68° C. |
| temperature $T_2$: | around 145° C. |
| volume flow $v_2$: | around 10.8 liter/bottle 9.7 Nm³/h |
| steam pressure: | around 1.0 bar |
| air pressure: | around 1.5 bar |

Activation Phase—Process Step 2

| | |
|---|---|
| container temperature $T_{BW}$: | around 67° C.-68° C. |
| volume flow $v_3$: | around 10.8 liter/bottle around 9.7 Nm3/h |
| temperature $T_2 > T_3$ | around 100° C. | depending on wall thickness and material
Addition of Sterile Air at Ambient Temperature The treatment times per activation phase are less than 10 seconds, while the treatment times x and y can be different, but also the same. Furthermore, it is possible to provide a treatment pause of, say, around four to five seconds between the application phase and the activation phase, i.e., the first process step of the activation phase is then initiated with a time delay of around five seconds, for example, after the introducing of the hydrogen peroxide sterilization medium or after the close of the application phase.

The present application has been described above by one sample embodiment. Of course, many changes and modifications are possible, without thereby leaving the basic notion of the present application. Thus, it was assumed above that the treatment heads 6 are part of a treatment machine or device of rotary design. Naturally, the method of the present application can also be carried out on layouts that are configured as linear machines. Furthermore, it was assumed above that the introducing of the hydrogen peroxide sterilization medium and the introducing of the activation medium are each done via the identical treatment head 6. Naturally, different treatment heads can also be used in these process steps.

A method is disclosed for sterilizing bottles, cans or similar containers by introducing hydrogen peroxide in the form of vapor or a hot hydrogen peroxide sterilization medium into each container during an application phase, and by activating the hydrogen peroxide sterilization medium in an activation phase by introducing a hot, sterile activation medium in the form of a gas and/or vapor into each container, in one possible embodiment by introducing hot sterile air into each container.

In at least one embodiment of the present disclosure, rotor 6 is configured to dispose a plurality of activator heads. For example, a single rotor 6 may be configured to treat up to 70,000 bottles per hour, or even more. In at least one embodiment, a controller may be disposed to control the temperature and volume of each pulse of activation medium with respect to a sensed temperature. The controller may be configured to provide starting point data such as initial starting temperatures and volumes of the portions or volumes of the activation medium used to activate the treatment agent. Also, the sensed temperature of the outside of the container may lag behind the actual temperature of the treatment agent inside the container. Therefore, the controller may be configured to control the temperatures and volumes of the pulses of activation medium by taking into account a lag time which may be present. Further, during periods between pulses or when the flow of activating medium is reduced, the treatment agent may continue to react or clean which may increase the temperature of the container being treated. Therefore, the controller may be configured to anticipate a rise in temperature of the treatment agent during a reduction and/or cessation in flow of the activating medium and control the flow of activating medium accordingly. In another embodiment, the rotation of the rotor and movement of ambient air about the containers being cleaned cools the containers. Therefore, the controller may also be configured to take into account cooling of the containers being treated, by ambient air.

In at least one embodiment of the present disclosure, the temperature of the container being treated is kept below a temperature which may distort the container outside of predetermined tolerances. These predetermined tolerances may be shape, dimension, and/or volume tolerances, for example. In at least one embodiment, the predetermined tolerances are maintained to virtually eliminate jamming of the treatment, filling, and closing machines in the filling plant. Predetermined tolerances are also maintained to minimize leaking containers, minimize difficulty in closing containers by assuring screw tops properly fit the treated container, and minimizing variations in the size and shape of the treated containers.

Figure 4:
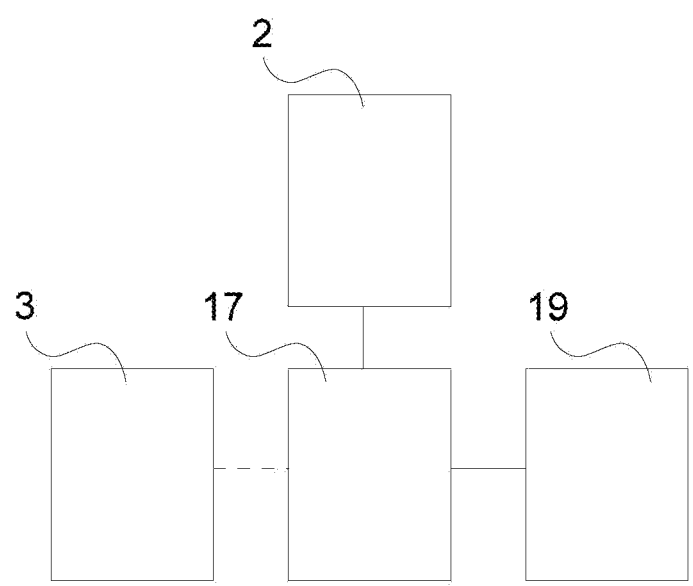
FIG. 4 shows a box drawing of components of a possible embodiment.
Figure 5:
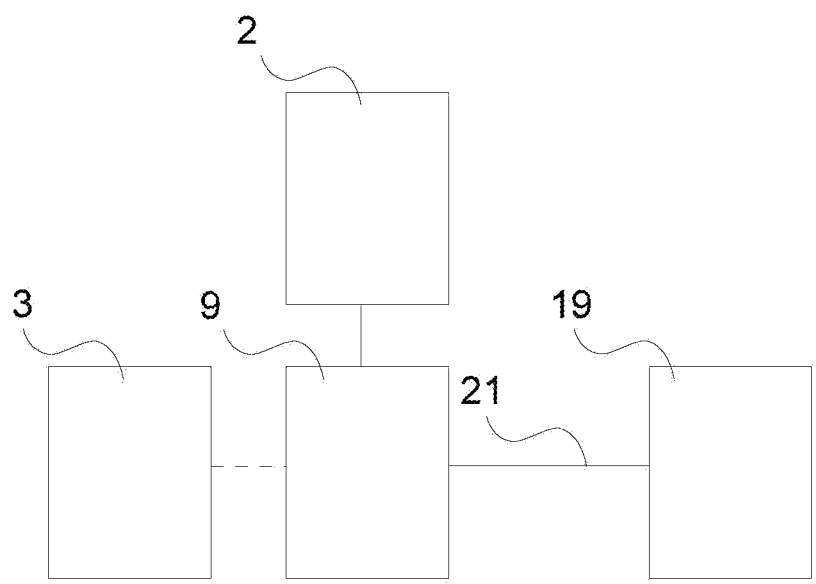
FIG. 5 shows a box drawing of components of a possible embodiment.
Figure 6:
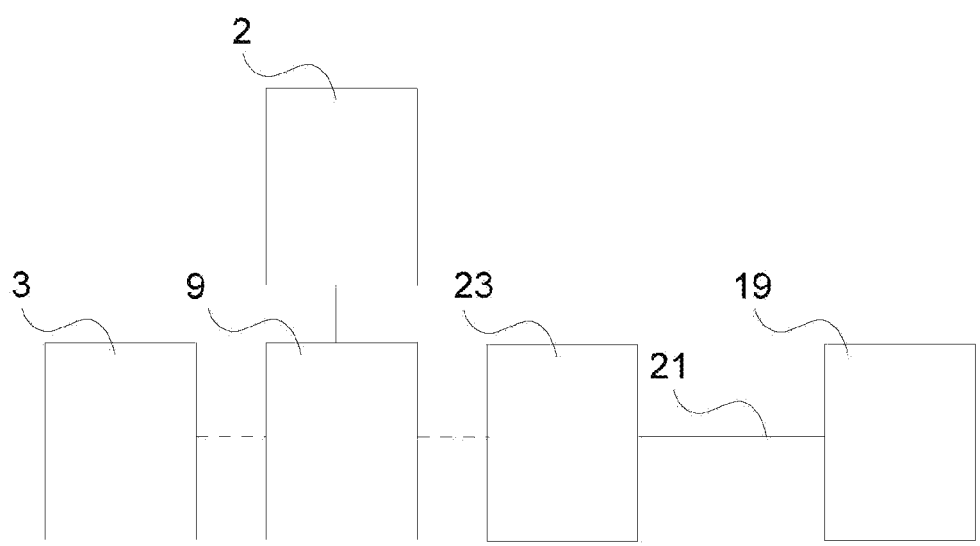
FIG. 6 shows a box drawing of components of a possible embodiment.

FIG. 4 shows a box drawing of components of a possible embodiment. Cooling supply 19 supplies coolant medium to coolant sleeves 17 mounted on rotor 2 to cool containers 3. FIG. 5 shows a box drawing of components of a possible embodiment. Cooling supply 19 supplies coolant medium to activator head 9 via coolant medium supply conduit 21 to cool the activation medium by admixture of coolant medium, which supply conduit comprises a valve or throttle to control the flow of coolant medium. FIG. 6 shows a box drawing of components of a possible embodiment. FIG. 6 is similar to FIG. 5, except a coolant unit 23 indirectly cools the activation medium.

Figure 3:
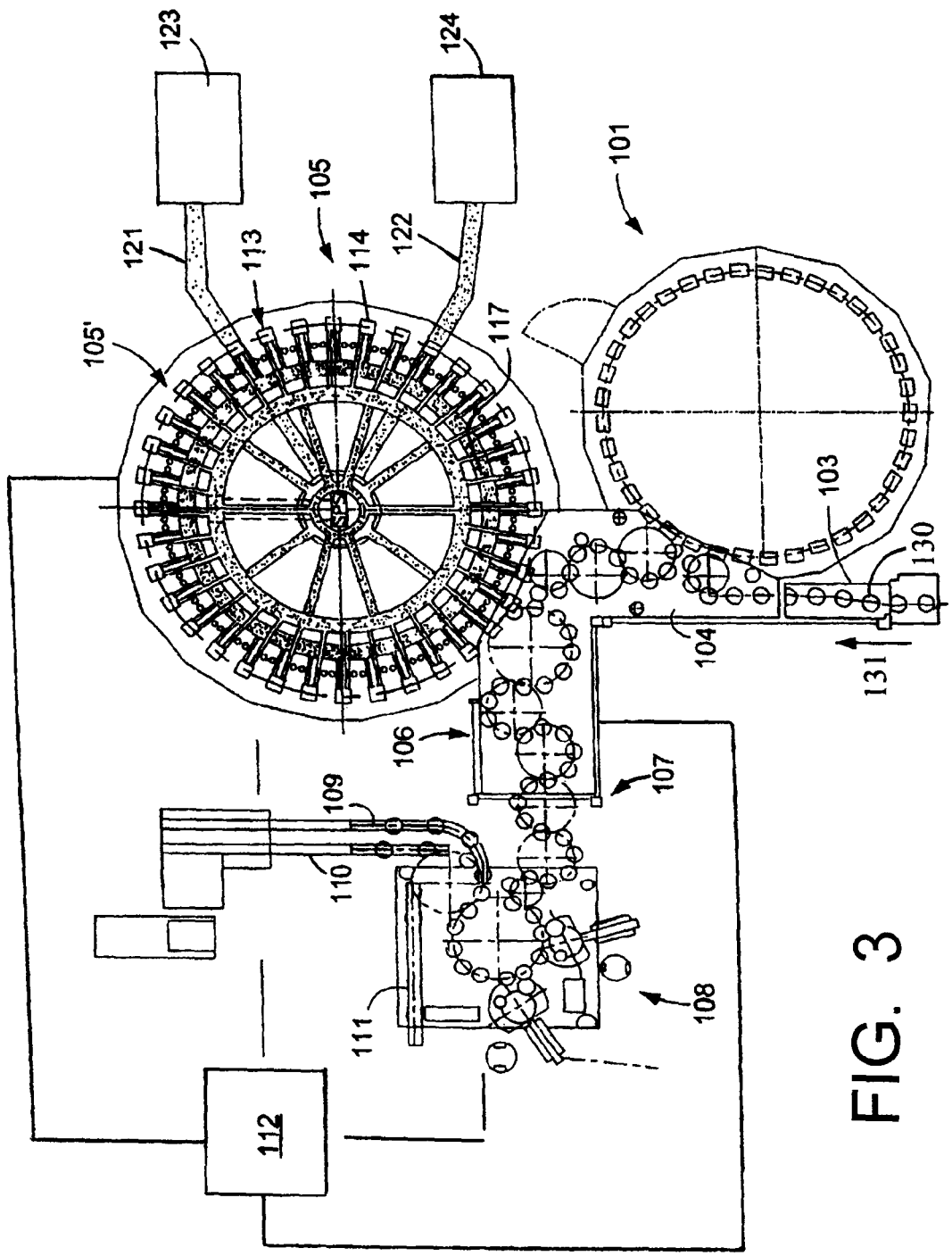
FIG. 3 shows schematically the main components of one possible embodiment example of a system for filling containers, specifically, a beverage bottling plant for filling bottles with at least one liquid beverage, in accordance with at least one possible embodiment.

FIG. 3 shows schematically the main components of one possible embodiment example of a system for filling containers, specifically, a beverage bottling plant for filling bottles 130 with at least one liquid beverage, in accordance with at least one possible embodiment, in which system or plant could possibly be utilized at least one aspect, or several aspects, of the embodiments disclosed herein.

FIG. 3 shows a rinsing arrangement or rinsing station 101, to which the containers, namely bottles 130, are fed in the direction of travel as indicated by the arrow 131, by a first conveyer arrangement 103, which can be a linear conveyor or a combination of a linear conveyor and a starwheel. Downstream of the rinsing arrangement or rinsing station 101, in the direction of travel as indicated by the arrow 131, the rinsed bottles 130 are transported to a beverage filling machine 105 by a second conveyer arrangement 104 that is formed, for example, by one or more starwheels that introduce bottles 130 into the beverage filling machine 105.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 3, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles 130 to different locations.

The first output conveyer arrangement 109, in the embodiment shown, is designed to convey bottles 130 that are filled with a first type of liquid beverage supplied by, for example, the supply reservoir 123. The second output conveyer arrangement 110, in the embodiment shown, is designed to convey bottles 130 that are filled with a second type of liquid beverage supplied by, for example, the supply reservoir 124. The third output conveyer arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyer arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

One feature or aspect of an embodiment is believed at the time of the filing of this patent application to possibly reside broadly in a method for the sterilization of bottles, cans or similar containers 3 by introducing a hot hydrogen peroxide sterilization medium into the containers 3 in an application phase and by activation of the hydrogen peroxide sterilization medium in an activation phase by introducing a sterile gaseous and/or vaporous hot activation medium, in one possible embodiment by introducing hot sterile air into the respective container 3, wherein the activation phase has at least two activation steps and in at least in the last activation step in terms of time the temperature of the volume flow $v_3$ of the activation medium supplied to the respective container 3 is regulated as a function of the container temperature $T_{BW}$ or the temperature of the wall of the container 3.

Another feature or aspect of an embodiment is believed at the time of the filing of this patent application to possibly reside broadly in the method, wherein the temperature regulation is done by indirect cooling of the volume flow $v_3$ of the second activation phase.

Yet another feature or aspect of an embodiment is believed at the time of the filing of this patent application to possibly reside broadly in the method, wherein the temperature regulation is done by direct cooling of the volume flow $v_3$ of the second activation phase, by mixing in a regulated volume flow $v_4$ of cooler gas in the volume flow $v_3$, and the gas in one possible embodiment is taken from the group of: sterile air, $CO_2$, $N_2$, noble gases or a mixture of these.

Still another feature or aspect of an embodiment is believed at the time of the filing of this patent application to possibly reside broadly in the method, wherein the temperature of the volume flow $v_2$, $v_3$ is regulated such that the container temperature $T_{BW}$ corresponds to a nominal temperature Nominal-$T_{BW}$.

A further feature or aspect of an embodiment is believed at the time of the filing of this patent application to possibly reside broadly in the method, wherein the container temperature $T_{BW}$ is measured in a noncontact manner.

Another feature or aspect of an embodiment is believed at the time of the filing of this patent application to possibly reside broadly in the method, wherein the container temperature $T_{BW}$ is measured with a pyrometer.

Yet another feature or aspect of an embodiment is believed at the time of the filing of this patent application to possibly reside broadly in the method, wherein, in the first activation step in time, the volume flow $v_2$ of the activation medium supplied to the respective container 3 is regulated as a function of the container temperature $T_{BW}$.

Still another feature or aspect of an embodiment is believed at the time of the filing of this patent application to possibly reside broadly in the method, wherein, in the first activation step in time, the supplying of the activation medium to the respective container 3 is controlled in time at constant or substantially constant temperature $T_2$ or essentially constant temperature and at constant or substantially constant volume flow $v_2$.

A further feature or aspect of an embodiment is believed at the time of the filing of this patent application to possibly reside broadly in the method, wherein the hot sterilization medium is supplied at constant or substantially constant temperature $T_1$ controlled in time to the respective container 3 in the application phase.

Another feature or aspect of an embodiment is believed at the time of the filing of this patent application to possibly reside broadly in the method, wherein, during the application phase, the hot sterilization medium is supplied to the respective container 3 at constant or essentially constant temperature and over a constant or essentially constant time period with a volume flow $v_1$ that is graduated or controlled in consideration of the container temperature $T_{BW}$ so that the container temperature $T_{BW}$ remains distinctly below the temperature $T_1$ of the hot hydrogen peroxide sterilization medium.

Yet another feature or aspect of an embodiment is believed at the time of the filing of this patent application to possibly reside broadly in the method, wherein the supplying of the hot hydrogen peroxide sterilization medium during the application phase occurs with an application duration of two and one half seconds to four seconds.

Still another feature or aspect of an embodiment is believed at the time of the filing of this patent application to possibly reside broadly in the method, wherein the treatment duration of an activation step is less than ten seconds.

A further feature or aspect of an embodiment is believed at the time of the filing of this patent application to possibly reside broadly in the method, wherein the activation phase is carried out at a single activator.

One feature or aspect of an embodiment is believed at the time of the filing of this patent application to possibly reside broadly in a sterilization device for containers 3 such as bottles, cups, cans and the like, to carry out the method according to the present application, with at least one activator head for introducing the hot activation medium into the containers 3, wherein this has at least one device for noncontact temperature measurement of surfaces of solid bodies and an interconnected computer-supported control and regulation mechanism, and this for evaluation of measured values and for regulation of the temperature and/or volume flow of the activation medium supplied to the respective container 3 at least in a last activation step in time of an activation phase having at least two activation steps as a function of the container temperature $T_{BW}$ or the temperature of the wall of the container 3.

Another feature or aspect of an embodiment is believed at the time of the filing of this patent application to possibly reside broadly in the sterilization device, wherein, on or in the vicinity of at least some of the activator heads 9, devices are arranged for the noncontact temperature measurement of surfaces of solid bodies, and in one possible embodiment one device for the noncontact temperature measurement of surfaces of solid bodies is arranged on or in the vicinity of each activator head 9.

Yet another feature or aspect of an embodiment is believed at the time of the filing of this patent application to possibly reside broadly in the sterilization device, wherein the at least one device for the noncontact temperature measurement of surfaces of solid bodies is a pyrometer.

Still another feature or aspect of an embodiment is believed at the time of the filing of this patent application to possibly reside broadly in the sterilization device, wherein at least one throttle, valve or the like is provided in the conduit of at least one cooling medium for the indirect regulation of the temperature by admixture and/or a cooling unit for the indirect cooling is arranged in this conduit.

A further feature or aspect of an embodiment is believed at the time of the filing of this patent application to possibly reside broadly in the sterilization device, wherein at least one throttle, valve or the like is arranged in each conduit of cooling medium upstream from the respective activator heads 9 and/or a cooling unit for the indirect cooling is arranged in each of these conduits.

Another feature or aspect of an embodiment is believed at the time of the filing of this patent application to possibly reside broadly in the sterilization device, comprising at least one tube 10 for the supplying of the activation medium, and a cooling sleeve is provided on the rotor 10, which at least partly encloses the containers being treated, and the cooling sleeve does not lie against the surface of the container or if so partly against it, so that an annular gap or channels are formed between container and sleeve when operating according to design.

Yet another feature or aspect of an embodiment is believed at the time of the filing of this patent application to possibly reside broadly in the sterilization device, wherein the sleeve has at least one opening that is connected to a conduit and a gas delivery device, by which a gaseous and/or liquid medium can be brought into the annular gap or the channels for cooling of the container wall.

Still another feature or aspect of an embodiment is believed at the time of the filing of this patent application to possibly reside broadly in the sterilization device, wherein the sleeve has at least one opening, which is connected to a conduit and a vacuum pump, by which ambient air can be brought into the annular gap or the channels for cooling the container wall and taken away.

One feature or aspect of an embodiment is believed at the time of the filing of this patent application to possibly reside broadly in a method of operating a container filling plant for filling plastic containers with a filling material, the method comprising steps to minimize distortion of plastic containers to be filled and maximize throughput of plastic containers by controlling the temperature of a container to be filled, said container filling plant comprising: a controller arrangement disposed and configured to monitor and control said container filling plant and to regulate control valves controlling a flow of activation medium; a filling machine being configured and disposed to fill empty plastic containers with a filling material; a first moving arrangement being configured and disposed to move plastic containers to said filling machine; a closing machine being configured and disposed to close filled plastic containers; a second moving arrangement being configured and disposed to accept filled plastic containers from said filling machine and to move filled plastic containers out of said filling machine and to said closing machine; a rotary treatment machine being configured and disposed to treat plastic containers prior to filling; a third moving arrangement being configured and disposed to move plastic containers to said treatment machine; said first moving arrangement being configured and disposed to move treated plastic containers from said treatment machine to said filling machine; said treatment machine comprising: at least one treatment device being configured and disposed to treat plastic containers upon the plastic containers being within said treatment machine; and said at least one treatment device comprising: a source of a treatment agent, which treatment agent is configured to be heated to treat the inside surface of a plastic container to be treated; a heater being configured and disposed to heat said treatment agent to a predetermined temperature, above a temperature of a container to be treated; a dispensing arrangement being configured to dispense heated treatment agent in a plastic container, which heated treatment agent is in sufficient amount and at a sufficient temperature to sufficiently coat the inside surface of the plastic container with condensed treatment agent to treat the plastic container, upon contact of said heated treatment agent on the inside surface of the container being treated; said dispensing arrangement also being configured to dispense a first and a second volume of heated activation medium in the plastic container, which heated activation medium is at a temperature sufficient to activate said condensed treatment agent; and a non-contact temperature measuring apparatus configured and disposed to sense a temperature, on or within the outer surface, of the plastic container being treated and to send said sensed temperature to said controller arrangement; said method comprising the steps of moving a plastic container in said treatment machine to be treated; heating said treatment agent to a temperature greater than a temperature of the plastic container to be treated, said treatment agent comprising hydrogen peroxide; dispensing said heated treatment agent into the plastic container being treated in an amount sufficient to coat the inside surface of the plastic container with a sufficient amount of condensate of said treatment agent to treat the plastic container; condensing at least a portion of said treatment agent on the inside surface of the plastic container being treated and coating the inside surface of the plastic container being treated with a sufficient amount of condensate to sufficiently clean the container to increase the shelf life of contents of the filled container to a substantially predetermined shelf life; dispensing a first volume of heated activation medium, comprising sterilized air, at a first temperature into the plastic container being treated, said first temperature being sufficient to heat said treatment agent to a temperature sufficient to treat the plastic container and to heat the container to be filled to just below a predetermined container temperature, said predetermined container temperature being a temperature at which the plastic container being treated will distort outside of predetermined tolerances; sensing a temperature on or within the outer surface of the plastic container being treated with said non-contact temperature measuring apparatus; sending said sensed temperature to said controller arrangement; controlling said first temperature of heated activation medium being dispensed into the plastic container being treated to a temperature sufficient to heat said treatment agent to a temperature sufficient to treat the plastic container and heat the container to be filled to a temperature just below said predetermined container temperature; reducing said flow of heated activation medium in the plastic container being treated, upon or just before the container to be filled reaching said predetermined container temperature, by an amount sufficient to permit cooling, during rotation of the plastic container in said treatment machine; dispensing a second volume of heated activation medium, comprising sterilized air, at a second temperature into the already heated plastic container being treated; sensing a temperature on or within the outer surface of the plastic container being treated with said non-contact temperature measuring apparatus; sending said sensed temperature to said controller arrangement; controlling said second temperature of said second volume of heated activation medium being dispensed in the plastic container being treated to a temperature sufficient to heat said treatment agent to a temperature sufficient to treat the plastic container and heat the container to be filled to a temperature just below said predetermined container temperature, said second temperature of second volume of heated activation medium being lower than said first temperature of said first volume of activation medium and at essentially the same volume as said first volume of activation medium, said second temperature being sufficient to activate said treatment agent to finally clean the container being treated and increase the shelf life of contents of the filled container to a substantially predetermined shelf life and to keep the temperature of the plastic container being treated below the predetermined temperature at which the plastic container will distort outside of predetermined tolerances; moving the treated plastic container from said dispensing arrangement to said filling machine; filling the treated plastic container; moving the treated, filled plastic container to said closing machine; closing the treated, filled plastic container.

Another feature or aspect of an embodiment is believed at the time of the filing of this patent application to possibly reside broadly in a method of operating a container filling plant for filling plastic containers with a filling material further comprising one of a), b), c), d), e), and f): a) said non-contact temperature measuring apparatus is a pyrometer; b) said non-contact temperature measuring apparatus is a pyrometer; and controlling the temperature of the heated treatment agent at a substantially constant temperature c) said non-contact temperature measuring apparatus is a pyrometer; controlling the temperature of the heated treatment agent at a substantially constant temperature; and controlling the volume of the heated treatment agent to keep a temperature of the plastic container being sterilized below the temperature at which the plastic container will distort outside of predetermined tolerances; d) said non-contact temperature measuring apparatus is a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; e) said non-contact temperature measuring apparatus is a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; and all said steps of treating a single plastic container are carried out in less than about 10 seconds; and f) said non-contact temperature measuring apparatus is a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; all said steps of treating single plastic container are carried out in less than about 10 seconds; and said step of disposing said first volume of heated activation medium into the plastic container being treated and step of disposing said second volume of heated activation medium into the plastic container being treated are carried out with a single activator.

Yet another feature or aspect of an embodiment is believed at the time of the filing of this patent application to possibly reside broadly in a method of sterilizing plastic containers wherein said step of controlling said second temperature of said second volume of heated activation medium being dispensed in the plastic container being treated comprises one of a) and b): a) controlling said second temperature of said second volume of heated activation medium with a heat exchanger; and b) controlling said second temperature of said second volume of heated activation medium by adding a controlled amount of cool sterilized air.

Still another feature or aspect of an embodiment is believed at the time of the filing of this patent application to possibly reside broadly in a method of sterilizing plastic containers comprising a cooling sleeve on said rotor disposed to at least partly surround a plastic container being treated, said cooling sleeve being configured to control the flow of a gaseous or liquid cooling medium about the outside surface of the container being treated.

A further feature or aspect of an embodiment is believed at the time of the filing of this patent application to possibly reside broadly in a method of treating plastic containers comprising the steps of: dispensing a heated treatment agent into a plastic container being treated in an amount and temperature sufficient to condense and coat the inside surface of the plastic container, with a sufficient amount of condensate to treat the plastic container; condensing at least a portion of said heated treatment agent on the inside surface of the plastic container being treated and coating the inside surface of the plastic container being treated with a sufficient amount of condensate to sufficiently clean the container; dispensing a first volume of heated activation medium at a first temperature into the plastic container being treated, said first temperature being sufficient to heat said treatment agent to a temperature sufficient to treat the plastic container; dispensing a second volume of heated activation medium at a second temperature in the already heated plastic container being treated; sensing a temperature on or within the outer surface of the plastic container being treated, upon dispensing said second volume of heated activation medium, with a temperature measuring apparatus; controlling said second temperature of said second volume of heated activation medium being dispensed in the plastic container being treated, to produce a temperature sufficient to heat said treatment agent to a temperature sufficient to treat the plastic container and keeping said temperature of the container to be filled below a predetermined container temperature, said predetermined container temperature being a temperature at which the plastic container will distort outside of predetermined tolerances, said second volume of heated activation medium producing a temperature lower than said first temperature of said first volume of activation medium.

Another feature or aspect of an embodiment is believed at the time of the filing of this patent application to possibly reside broadly in a method of treating plastic containers further comprising the step of: cooling a part of said second volume of heated activation medium, said cooling comprising one of a) and b): a) cooling said part of said second volume of heated activation medium with a heat exchanger; b) cooling said part of said second volume of heated activation medium by adding a controlled amount of cool sterilized air.

Yet another feature or aspect of an embodiment is believed at the time of the filing of this patent application to possibly reside broadly in a method of treating plastic containers further comprising one of a), b), c), d), e), f), and g): a) said step of sensing said temperature on or within the outer surface of the plastic container being treated comprises sensing said temperature without contacting the plastic container being sterilized; b) said step of sensing said temperature on or within the outer surface of the plastic container being treated comprises sensing said temperature with a pyrometer; c) said step of sensing said temperature on or within the outer surface of the plastic container being treated comprises sensing said temperature with a pyrometer; and controlling the temperature of the heated treatment agent at a substantially constant temperature; d) said step of sensing said temperature on or within the outer surface of the plastic container being treated comprises sensing said temperature with a pyrometer; controlling the temperature of the heated treatment agent at a substantially constant temperature; and controlling the volume of the heated treatment agent to keep a temperature of the plastic container being sterilized below the temperature at which the plastic container will distort outside of predetermined tolerances; e) said step of sensing said temperature on or within the outer surface of the plastic container being treated comprises sensing said temperature with a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; f) said step of sensing said temperature on or within the outer surface of the plastic container being treated comprises sensing said temperature with a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; and all said steps of treating a single plastic container are carried out in less than about 10 seconds; and g) said step of sensing said temperature on or within the outer surface of the plastic container being treated comprises sensing said temperature with a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; all said steps of treating single plastic container are carried out in less than about 10 seconds; and said step of disposing said first volume of heated activation medium into the plastic container being treated and step of disposing said second volume of heated activation medium into the plastic container being treated are carried out with a single activator.

Still another feature or aspect of an embodiment is believed at the time of the filing of this patent application to possibly reside broadly in a method of treating plastic containers further comprising the steps of: sensing a third temperature, prior to said step of dispensing a second volume, on or within the outer surface of the plastic container being treated; sending said sensed third temperature to a controller arrangement; and controlling the volume of said first volume of heated activation medium, as a function of said third sensed temperature, during said step of dispensing said first volume of heated sterilized air into the plastic container being treated.

A further feature or aspect of an embodiment is believed at the time of the filing of this patent application to possibly reside broadly in a method of sterilizing containers such as plastic containers, bottles, or other containers, said method comprising the steps of: dispensing a heated sterilizing agent comprising hydrogen peroxide into a container being sterilized in an amount and at a temperature sufficient to condense and coat the inside surface of the container, with a sufficient amount of condensate to sterilize the container condensing at least a portion of said sterilizing agent on the inside surface of the container being sterilized, and coating the inside surface of the container being sterilized with a sufficient amount of condensate to sufficiently sterilize the container; determining a first portion of heated sterilized air to heat said sterilizing agent to a temperature sufficient to sterilize the container and keep a temperature of the container being sterilized below the temperature at which the container will distort outside of predetermined tolerances; disposing said first determined portion of heated sterilized air into the container being sterilized, said first determined portion being sufficient to heat said sterilizing agent to a temperature sufficient to sterilize the container and keep a temperature of the container being sterilized below the temperature at which the container will distort outside of predetermined tolerances; reducing said flow of said first determined portion of heated sterilized air in the container being sterilized; determining a second portion of heated sterilized air to heat said sterilizing agent to a temperature sufficient to sterilize the container and keep a temperature of the container being sterilized below the temperature at which the container will distort outside of predetermined tolerances; disposing said second determined portion of heated sterilized air into the already heated container being sterilized, the container having been already heated by said first determined portion of heated sterilized air, said second determined portion being sufficient to heat said sterilizing agent to a temperature sufficient to finally sterilize the container and keep a temperature of the container being sterilized below the temperature at which the container will distort outside of predetermined tolerances; lowering the temperature of the container being sterilized, subsequent to said step of reducing said flow of said first determined portion of heated sterilized air, and prior to said final sterilization by said second determined portion of heated sterilized air.

Another feature or aspect of an embodiment is believed at the time of the filing of this patent application to possibly reside broadly in a method of sterilizing containers further comprising the steps of: sensing a first temperature, subsequent to said step of reducing said flow of said first determined portion of heated sterilized air, on or within the outer surface of the container being sterilized; sending said sensed first temperature to a controller arrangement; said step of determining said second portion of heated sterilized air being carried out with said controller arrangement and comprising; determining a temperature of said second portion of heated sterilized air as a function of said first sensed temperature; controlling the temperature of said second determined portion of heated sterilized air during said step of disposing said second determined portion of heated sterilized air into the container being sterilized; and said second controlled portion of sterilized heated air being controlled, with said controller arrangement, at said temperature determined as a function of said first sensed temperature.

Yet another feature or aspect of an embodiment is believed at the time of the filing of this patent application to possibly reside broadly in a method of sterilizing containers further comprising the step of: cooling a part of said second determined portion of heated sterilized air, said cooling being carried out after said step of determining a temperature of said second portion of heated sterilized air as a function of said first sensed temperature.

One feature or aspect of an embodiment is believed at the time of the filing of this patent application to possibly reside broadly a method of sterilizing containers wherein said step of cooling a part of said second determined portion of heated sterilized air comprises one of a) and b): a) cooling said part of said second determined portion of heated sterilized air with a heat exchanger; b) cooling said part of said second determined portion of heated sterilized air by adding a controlled amount of cool sterilized air.

Another feature or aspect of an embodiment is believed at the time of the filing of this patent application to possibly reside broadly in a method of sterilizing containers wherein said step of sensing said first temperature on or within the outer surface of the container being sterilized comprises sensing said first temperature without contacting the container being sterilized.

Yet another feature or aspect of an embodiment is believed at the time of the filing of this patent application to possibly reside broadly in a method of sterilizing containers wherein said step of sensing said first temperature on or within the outer surface of the container being sterilized comprises sensing said first temperature of the container being sterilized with a pyrometer.

Still another feature or aspect of an embodiment is believed at the time of the filing of this patent application to possibly reside broadly in a method of sterilizing containers further comprising the steps of: sensing a second temperature, prior to said step of reducing said flow of said first determined portion of heated sterilized air, on or within the outer surface of the container being sterilized; sending said second sensed temperature to said controller arrangement; said step of determining said first portion of heated sterilized air being carried out with said controller arrangement and comprising; determining a volume of said first portion of heated sterilized air as a function of said second sensed temperature; controlling the volume of said first determined portion of heated sterilized air during said step of disposing said first determined portion of heated sterilized air into the container being sterilized; and said first controlled portion of sterilized heated air being controlled, with said controller arrangement, at said volume determined as a function of said second sensed temperature.

A further feature or aspect of an embodiment is believed at the time of the filing of this patent application to possibly reside broadly in a method of sterilizing containers wherein said step of disposing said first determined portion of heated sterilized air into the container being sterilized comprises controlling said first determined portion of heated sterilized air to a substantially constant volume flow rate at a substantially constant temperature.

Another feature or aspect of an embodiment is believed at the time of the filing of this patent application to possibly reside broadly in a method of sterilizing containers wherein said step of dispensing a heated sterilizing agent comprising hydrogen peroxide into a container being sterilized further comprises one of a), b), and c): a) controlling the temperature of the heated sterilizing agent at a substantially constant temperature; b) controlling the temperature of the heated sterilizing agent at a substantially constant temperature; and controlling the volume of the heated sterilizing agent to keep a temperature of the container being sterilized below the temperature at which the container will distort outside of predetermined tolerances; and c) controlling the temperature of the heated sterilizing agent at a substantially constant temperature; controlling the volume of the heated sterilizing agent to keep a temperature of the container being sterilized below the temperature at which the container will distort outside of predetermined tolerances; and controlling the time period of said step of dispensing a heated sterilizing agent into a container being sterilized between a range of about 2.5 seconds to about 4 seconds.

Yet another feature or aspect of an embodiment is believed at the time of the filing of this patent application to possibly reside broadly in a method of sterilizing containers wherein all said steps of sterilizing a single container are carried out in less than about 10 seconds.

Still another feature or aspect of an embodiment is believed at the time of the filing of this patent application to possibly reside broadly in a method of sterilizing containers wherein said step of disposing said first determined portion of heated sterilized air into the container being sterilized and step of disposing said second determined portion of heated sterilized air into the container being sterilized are carried out with a single activator.

A further feature or aspect of an embodiment is believed at the time of the filing of this patent application to possibly reside broadly in a method of sterilizing containers wherein the volume of said second determined portion of heated sterilized air disposed in the container being sterilized is substantially the same as the volume of said first portion of heated sterilized air being disposed in the container being sterilized.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the German Office Action dated Dec. 10, 2007 and/or cited elsewhere are hereby incorporated by reference as if set forth in their entirety herein as follows: DE 10 2004 030 956, having the following English translation of the German title "Sterilization of containers, especially plastics bottles for drinks, by blowing in hydrogen peroxide vapor and hot air then blowing in air at sufficiently high flow rate to avoid excessive container temperature," published on Jan. 12, 2006; EP 0 590 505, having the following English translation of the German title "Apparatus and control for heat treatment and sterilizing of bottles or containers," published on Apr. 6, 1994; DE 10 2005 018 382, having the following English translation of the German title "Bottle washing machine, for cleaning bottles carried through on conveyor, measures final bottle temperatures to determine that hot detergent has been fully rinsed clear by cold water," published on Oct. 26, 2006; DE 198 46 322, having the following English translation of the German title "Monitoring treatment of internal vol. of bottles or vessels by rinser involves detecting flow of fluid introduced into interior of bottle, as it emanates from open mouth of bottle," published on Apr. 13, 2000; DE 199 49 692, having the following English translation of the German title "Sterilization of temperature-sensitive especially polyethylene terephthalate bottles moving on a conveyor, using a peroxide aerosol and sterile air," published on Apr. 19, 2001; and WO 2006/053745, having the following English translation of the German title "PROCESS AND DEVICE FOR STERILISING CONTINUOUSLY CONVEYED PLASTIC BOTTLES," published on May 26, 2006.

All of the patents, patent applications or patent publications, which were cited in the International Search Report dated Jul. 29, 2008, and/or cited elsewhere are hereby incorporated by reference as if set forth in their entirety herein as follows: DE 199 49 692, having the following English translation of the German title "Sterilization of temperature-sensitive especially polyethylene terephthalate bottles moving on a conveyor, using a peroxide aerosol and sterile air," published on Apr. 19, 2001; DE 10 2004 030 956, having the following English translation of the German title "Sterilization of containers, especially plastics bottles for drinks, by blowing in hydrogen peroxide vapor and hot air then blowing in air at sufficiently high flow rate to avoid excessive container temperature," published on Jan. 12, 2006; DE 10 2004 030 957, having the following English translation of the German title "Method of sterilising bottles or similar containers, and steriliser for carrying out the method," published on Jan. 12, 2006; EP 0 590 505, having the following English translation of the German title "Apparatus and control for heat treatment and sterilizing of bottles or containers," published on Apr. 6, 1994; and US 2006/032189, having the title "Process and method of sterilizing aseptic containers," published on Feb. 16, 2006.

Also, hereby incorporated by reference as if set forth in their entirety herein are US Patent Application WIPO patent publication no. WO/2008/135132. US Patent Application is a Continuation-In-Part application of WO/2008/135132, having International Patent Application No. PCT/EP2008/002858, filed on Apr. 11, 2008, which claims priority from Federal Republic of Germany Patent Application No. 10 2007 020 458.4, filed on Apr. 27, 2007.

Some examples of non-contact temperature measuring devices or pyrometers that may possibly be utilized or adapted for use in at least one possible embodiment may possibly be found in the following: those temperature measuring devices manufactured and sold by Clark Pyrometers, 10 Brent Dr., Hudson Mass.; those manufactured and sold by Radiant Innovation, HsinChu, Taiwan; those manufactured and sold by Omega Engineering Inc., 1 Omega Drive, Stamford, Conn. Still other devices which may possibly be used in at least one possible embodiment of the present application may possibly include the optical pyrometer types disclosed in: Hartel U.S. Pat. No. 5,398,734 (KHS Machinen-und Anlagenban Aktiengesellschaft); Green U.S. Pat. No. 3,535,522 (Glass Container Industry Research) and Howell U.S. Pat. Nos. 2,987,589 and 2,869,369 (Servo Corp. of America), the disclosures of which are all hereby incorporated by reference as if set forth in their entirety herein. Some examples of infrared thermometers which may possibly be used in at least one possible embodiment of the present application may possibly be found in the following US patents: Heinke et al. U.S. Pat. No. 5,81,410, and Christol et al. U.S. Pat. No. 4,634,294 (both assigned to Raytek, Inc.), the disclosures of which are also all hereby incorporated by reference as if set forth in their entirety herein.

An example of a device configured to inject hydrogen peroxide into a container for sterilization, which may possibly be utilized or adapted for use in at least one possible embodiment of the present application, may possibly be found in the following U.S. Pat. No. 7,010,900, having the title "Beverage bottling plant for filling bottles with a liquid beverage filling material, and a cleaning device for cleaning bottles in a beverage bottling plant," published on Mar. 14, 2006.

The patents, patent applications, patent publications, and other publications listed herein are incorporated by reference in their entirety herein, except words relating to the opinions and judgments of the author and not directly relating to the technical details of the description of the embodiments therein are not incorporated by reference. The purpose of incorporating U.S. patents, Foreign patents, patent publications, and other publications is solely to provide additional information relating to technical features of one or more embodiments, which information may not be completely disclosed in the wording in the pages of this application. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not to be incorporated by reference herein.

The corresponding foreign and international patent publication applications, namely, Federal Republic of Germany Patent Application No. 10 2007 020 457.6, filed on Apr. 27, 2007, having inventors Daryoush SANGI and Thomas HEROLD, and DE-OS 10 2007 020 457.6 and DE-PS 10 2007 020 457.6, and International Application No. PCT/EP2008/003247, filed on Apr. 23, 2008, having WIPO Publication No. WO 2008/135165 and inventors Daryoush SANGI and Thomas HEROLD, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the corresponding foreign equivalent patent application(s), that is, PCT/EP2008/003247 and German Patent Application 10 2007 020 457.6, is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned word in this sentence, when not used to describe technical features of one or more embodiments, are not generally considered to be incorporated by reference herein.

Statements made in the original foreign patent applications PCT/EP2008/003247 and DE 10 2007 020 457.6 from which this patent application claims priority which do not have to do with the correction of the translation in this patent application are not to be included in this patent application in the incorporation by reference.

Any statements about admissions of prior art in the original foreign patent applications PCT/EP2008/003247 and DE 10 2007 020 457.6 are not to be included in this patent application in the incorporation by reference, since the laws relating to prior art in non-U.S. Patent Offices and courts may be substantially different from the Patent Laws of the United States.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A sterilization arrangement comprising:
   a first delivery arrangement to introduce hydrogen peroxide into a container;
   a second delivery arrangement to:
      introduce a heated gaseous and/or vaporous activation medium into a container at a first temperature in a first step; and
      subsequently introduce activation medium into the container at a second temperature, lower than a first temperature of the activation medium in the first step, in a second step;
   a monitoring arrangement to monitor, without contact, the temperature of the container or the wall of the container;
   a computer control arrangement to regulate said second temperature based on a monitored container or wall temperature; and
   one of (C) and (D):
      (C) at least one throttle or valve disposed in a coolant medium supply conduit and configured to regulate the temperature of activation medium by controlling admixture of coolant into said activation medium; and
      (D) a cooling unit disposed in a coolant medium supply conduit and configured to indirectly cool the temperature of activation medium.

2. The sterilization arrangement according to claim 1, wherein:
   said second delivery arrangement comprises at least one activator head for dispensing activation medium into containers; and
   said monitoring arrangement comprises at least one temperature detection device for contactless measurement of the surfaces of solid bodies, wherein each temperature detection device is positioned adjacent at least one of said at least one activator head.

3. The sterilization arrangement according to claim 2, wherein said at least one temperature detection device comprises a pyrometer.

4. The sterilization arrangement according to claim 3, wherein said sterilization arrangement comprises:
   a rotor and cooling sleeves disposed thereon;
   at least one tube configured to supply activation medium; and
   said cooling sleeves are configured to at least partly enclose containers being treated and form an annular gap or channels between the containers and said sleeves.

5. The sterilization arrangement according to claim 4, wherein each of said sleeves comprises at least one opening connected to a conduit and a gas delivery device, by which a gaseous and/or liquid medium can be brought into the annular gap or the channels for cooling of the container wall.

6. The sterilization arrangement according to claim 4, wherein each of said sleeves comprises at least one opening connected to a conduit and a vacuum pump, by which ambient air can be brought into the annular gap or the channels for cooling of the container wall.

7. The sterilization arrangement according to claim 1, wherein said sterilization arrangement comprises:
   a rotor and cooling sleeves disposed thereon;
   at least one tube configured to supply activation medium; and
   said cooling sleeves are configured to at least partly enclose containers being treated and form an annular gap or channels between the containers and said sleeves.

8. The sterilization arrangement according to claim 7, wherein each of said sleeves comprises at least one opening connected to a conduit and one of (G) and (H):
   (G) a gas delivery device, by which a gaseous and/or liquid medium can be brought into the annular gap or the channels for cooling of the container wall; and
   (H) a vacuum pump, by which ambient air can be brought into the annular gap or the channels for cooling of the container wall.

9. A method of sterilizing containers comprising:
   conducting heated or vaporous hydrogen peroxide into a container; and
   activating said hydrogen peroxide in said container in an activation phase comprising a first step and a second step subsequent to said first step;
   said first step comprising conducting heated gaseous and/or vaporous activation medium into said container;
   said second step comprising:
      conducting additional activation medium into said container at a second temperature, lower than a first temperature of said activation medium in said first step, while simultaneously monitoring a temperature of at least a portion of said container; and
      adjusting said second temperature, as needed based on the monitored temperature of said at least a portion of said container, and thereby both maintaining the temperature of said container below a temperature at which said container would be damaged, and maintaining the temperature of said hydrogen peroxide at or above an activation temperature, throughout said second step.

10. The method according to claim 9, wherein said step of adjusting said second temperature comprises directly cooling said activation medium by mixing in a flow of cooler gas comprising one of: sterile air, $CO_2$, $N_2$, noble gases, or a mixture thereof.

11. The method according to claim 10, wherein the container temperature is measured in a contactless manner.

12. The method according to claim 11, wherein the container temperature is measured using a pyrometer.

13. The method according to claim 12, wherein said first step comprises one of (A) and (B):
   (A) conducting said activation medium at a volume flow rate, and adjusting said volume flow rate based on the monitored container temperature; and
   (B) conducting said activation medium at a constant or essentially constant volume flow rate at a constant or essentially constant temperature.

14. The method according to claim 13, wherein said hydrogen peroxide is heated and supplied at a constant or essentially constant temperature over a constant or essentially constant time at a hydrogen peroxide volume flow rate that is controlled based on the monitored container temperature so that the container temperature remains substantially below the temperature of said hydrogen peroxide.

15. The method according to claim 14, wherein said hydrogen peroxide is supplied for a time of 2.5 to 4 seconds.

16. The method according to claim 15, wherein the duration of each of said first and second steps is less than 10 seconds.

17. The method according to claim 16, wherein said activation phase is performed by a single activator.

18. The method according to claim 9, wherein said step of adjusting said second temperature comprises indirectly cooling said activation medium using a cooling unit disposed in a coolant medium supply conduit.

* * * * *